United States Patent
Xu et al.

(10) Patent No.: US 9,404,855 B2
(45) Date of Patent: *Aug. 2, 2016

(54) METHOD TO OBTAIN ABSORPTION SPECTRA FROM NEAR-FIELD INFRARED SCATTERING USING HOMO-DYNE DETECTION

(71) Applicants: Xiaoji Xu, Toronto (CA); Gilbert C Walker, Mississauga (CA)

(72) Inventors: Xiaoji Xu, Toronto (CA); Gilbert C Walker, Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/647,410

(22) PCT Filed: Nov. 27, 2013

(86) PCT No.: PCT/CA2013/000990
§ 371 (c)(1),
(2) Date: May 26, 2015

(87) PCT Pub. No.: WO2014/082158
PCT Pub. Date: Jun. 5, 2014

(65) Prior Publication Data
US 2015/0308947 A1    Oct. 29, 2015

Related U.S. Application Data

(63) Continuation of application No. 13/835,181, filed on Mar. 15, 2013, now Pat. No. 8,646,110.

(60) Provisional application No. 61/730,201, filed on Nov. 27, 2012.

(51) Int. Cl.
*G01Q 20/02* (2010.01)
*G01Q 30/00* (2010.01)
(Continued)

(52) U.S. Cl.
CPC .............. *G01N 21/359* (2013.01); *B82Y 20/00* (2013.01); *G01B 9/0203* (2013.01); *G01Q 10/00* (2013.01);
(Continued)

(58) Field of Classification Search
CPC ............ G01N 21/359; G01N 2201/10; G01N 2201/06113; G01B 9/0203; G01Q 10/00; G01Q 60/22; G01Q 30/02; G01Q 60/24; B82Y 20/00; B82Y 35/00
See application file for complete search history.

(56) References Cited

U.S. PATENT DOCUMENTS

| 6,835,926 B2 | 12/2004 | Weitekamp et al. |
| 7,969,650 B2 | 6/2011 | Marks et al. |
| 8,646,110 B1 | 2/2014 | Xu et al. |

FOREIGN PATENT DOCUMENTS

EP    1770714    4/2007

OTHER PUBLICATIONS

Florian Huth et al., Nano-FTIR Absorption Spectroscopy of Molecular Fingerprints at 20 nm Spatial Resolution, Nano Lett. Dec. 2012, 3973-3978.

(Continued)

*Primary Examiner* — Brooke Purinton
(74) *Attorney, Agent, or Firm* — Lynn C. Schumacher; Stephen W. Leonard; Hill & Schumacher

(57) ABSTRACT

The present disclosure provides a procedure and an apparatus to obtain the absorption profiles of molecular resonance with ANSOM. The method includes setting a reference field phase to $\phi=0.5\pi$ relative to the near-field field, and reference amplitude $A \geq 5|\alpha_{eff}|$. The requirement on phase precision is found to be $<0.3\pi$. The apparatus includes a phase stabilization mechanism in addition to the ANSOM to maintain high phase precision homodyne phase condition of less than 0.1 rad. This method enables ANSOM performing vibrational spectroscopy at nanoscale spatial resolution.

26 Claims, 11 Drawing Sheets

(51) Int. Cl.
*G01N 21/359* (2014.01)
*B82Y 20/00* (2011.01)
*G01Q 30/02* (2010.01)
*G01Q 60/22* (2010.01)
*G01B 9/02* (2006.01)
*G01Q 10/00* (2010.01)

(52) U.S. Cl.
CPC ............... *G01Q 30/02* (2013.01); *G01Q 60/22* (2013.01); *G01N 2201/06113* (2013.01); *G01N 2201/10* (2013.01)

(56) References Cited

OTHER PUBLICATIONS

Xiaoji G. Xu et al., Pushing the Sample-Size Limit of Infrared Vibrational Nanospectroscopy: From Monolayer toward Single Molecule Sensitivity, J. Phys. Chem. Lett. Mar. 2012, 1836-1841.

F. Huth et al., Infrared-spectroscopic nanoimaging with a thermal source, Nature Materials, vol. 10, May 2011, 352-356.

Xiaoji G. Xu et al., Phase Controlled Homodyne Infrared Near-Field Microscopy and Spectroscopy Reveal Inhomogeneity within and among Individual Boron Nitride Nanotubes, J. Phys. Chem. A 2013, 117, 3348-3354.

Nenad Ocelic et al., Pseudoheterodyne detection for background-free near-field spectroscopy, Applied Physics Letters 89, 101124 (2006); doi: 10.1063/1.2348781.

International Search Report in PCT/CA2013/000990 dated Mar. 5, 2014.

Written Opinion in PCT/CA2013/000990 dated Mar. 5, 2014.

Thomas Taubner et al: "Effect of Tip Modulation on Image Contrast in Scattering-Type Near-Field Optical Microscopy", Journal of the Korean Physical Society, vol. 47, Aug. 1, 2005 pp. 213-216.

B. Deutsch et al: "Near-field amplitude and phase recovery using phase-shifting interferometry", Optics Express, vol. 16, No. 2, Jan. 1, 2008, p. 494.

Azoulay J et al: "Optical contrast in Apertureless Microscopy", applied Optics, Optical Society of America, Washington, DC; US, vol. 39 No. 1, Jan. 1, 2000, pp. 129-134.

US 9,404,855 B2

METHOD TO OBTAIN ABSORPTION SPECTRA FROM NEAR-FIELD INFRARED SCATTERING USING HOMO-DYNE DETECTION

CROSS REFERENCE TO RELATED U.S. PATENT APPLICATION

This patent application is a National Phase application claiming the benefit of the international PCT Patent Application No. PCT/CA2013/000990, filed on Nov. 27, 2013, in English, which relates to U.S. provisional patent application Ser. No. 61/730,201 filed on Nov. 27, 2012, and utility patent application U.S. Ser. No. 13/835,181 filed on Mar. 15, 2013, both entitled METHOD TO OBTAIN ABSORPTION SPECTRA FROM NEAR-FIELD INFRARED SCATTERING USING HOMODYNE DETECTION, filed in English, incorporated herein in their entireties by reference.

FIELD

The present invention relates to a method for obtaining absorption spectra from near-field infrared scattering using homodyne detection.

BACKGROUND

Apertureless near-field scanning optical microscopy (ANSOM) provides spatial resolution beyond the diffraction limit of light. However, there is a key issue with respect to ANSOM to resolve for some spectroscopic applications, namely: the directly detectable near-field scattering signal has dispersive profiles rather than absorptive profiles. The absorptive profiles are generally a collection of peaks on spectrum that are obtained from infrared (IR) absorption spectroscopy. Far field spectral banks with absorption profiles characteristic of chemical compounds have been created for chemical identifications. As a result, ANSOM is not yet a convenient tool for infrared nanospectroscopy due to its dispersive profiles and is unable to tap into the existing spectral banks that characterize macroscopic samples of materials to achieve nanoscale chemical identification.

There are currently several ways to obtain the desired absorptive profile in ANSOM implementations. One recent technique is called pseudo-heterodyne detection, and it relies on lock-in detection on the combination reference frequency of ANSOM tip oscillation and reference phase modulation (see Ocelic, N., A. Huber, and R. Hillenbrand, "*Pseudoheterodyne detection for background-free near-field spectroscopy*" Applied Physics Letters, 2006. 89(10)). While it obtains the phase of near-field scattered light, there are two disadvantages associated with the pseudo-heterodyne technique. The first one is the reduced signal level due to detection of weak sidebands instead of the main band in lock-in detection. The second potential drawback is that it measures the phase of near-field scattered signal instead of the imaginary part of the near-field. The equivalency of phase and imaginary part of near-field scattered signal is a good approximation under the condition that the real part of near-field scattering is strong, but the approximation is not always correct.

The second technique to obtain absorptive profile is to use a coherent broadband light source to do asymmetric Fourier transform infrared spectroscopy. This has been described in two articles, see Huth, F., et al., "Nano-FTIR Absorption Spectroscopy of Molecular Fingerprints at 20 nm Spatial Resolution", Nano Letters, 2012. 12(8): p. 3973-3978; and Xu, X. G., et al., "*Pushing the Sample-Size Limit of Infrared Vibrational Nanospectroscopy: From Monolayer toward Single Molecule Sensitivity*" The Journal of Physical Chemistry Letters, 2012. 3(13): p. 1836-1841. While it offers multiplex technique capability, this type of technique requires a coherent broadband light source that is expensive (~$300 k in 2012) and comes with low laser energy that intrinsically leads to low signal quality, which limits its practical applications.

SUMMARY

The present disclosure provides a procedure to obtain the absorption profiles of molecular resonance with ANSOM. An embodiment of the method includes setting a reference field phase most preferably to $\phi=0.57\pi$ (or $-0.5\pi$) relative to the near-field field, and reference amplitude $A \geq 5|\alpha_{eff}|$. The requirement on phase precision is found to be $<0.3\pi$. This method enables ANSOM performing vibrational spectroscopy on nanometer scale objects.

An embodiment disclosed herein is an apparatus for measuring an absorption spectrum of nanoscale objects, comprising:

a) a scanning atomic force microscope, a lock-in amplifier connected to said sample scanning atomic force microscope, a computer controller connected to said lock-in amplifier, a detector for detecting electromagnetic radiation connected to said lock-in amplifier, a coherent light source which emits a coherent beam of light;

b) an interferometer integrated with said atomic force microscope, said coherent light source and said detector, said interferometer having a reference arm and a sample arm, the interferometer being positioned for directing light along a sample arm from said coherent light source to a sample mounted on a scanning stage of said scanning atomic force microscope and for directing a light beam scattered from the sample and a scanning probe tip of said atomic force microscope into said detector, said interferometer also being positioned for directing a light beam along a reference arm from said coherent light source to a position adjustable reflector and directing a light beam reflected from said adjustable reflector to recombine with said scattered light beam into said detector;

c) a control circuit for adjusting and maintaining a position of the adjustable reflector to give an relative optical phase difference between said light beams in said reference arm and said sample arm to be in a range from about $0.4\pi$ to about $0.6\pi$, or $-0.4\pi$ to about $-0.6\pi$;

d) wherein said lock-in amplifier is configured to receive a reference frequency from said atomic force microscope and an output voltage signal from said detector and, based on said reference frequency and said output signal, demodulate said output voltage signal into harmonic components and relaying said second and higher harmonic components to said computer controller which is programmed with instructions to form an apertureless near-field scanning optical microscope image of said nanoscale objects.

Also disclosed herein is method of measuring an absorption spectrum of nanoscale objects, comprising:

a) rastering a nanoscale object under a scanning probe tip of a scanning atomic force microscope;

b) illuminating said nanoscale object and said scanning probe tip with a frequency tunable coherent light source along a sample arm of an interferometer;

c) combining a scattered coherent light beam from said nanoscale object and said scanning probe tip along said sample arm with a beam of light from said frequency tunable light source reflected from a reflector in a reference arm of the interferometer and directing the combined coherent light beams into a detector;

d) demodulating an output signal from said detector to give second or higher harmonic demodulation signals and, using the second or higher harmonic demodulation signals, adjusting a position of the adjustable reflector to give an optical phase difference between said light beams in said reference arm and said sample arm to be in a range from about $0.4\pi$ to about $0.6\pi$, or from about $-0.4\pi$ to about $-0.6\pi$, and maintaining said position using feedback to maintain the optical path difference; and e) obtaining an image of signal intensity being proportional to the imaginary part of infrared absorption coefficient of the sample through the combination of scanning probe microscopy and light scattering from a sharp scanning probe tip with said procedure of setting specific homodyne phase in the interferometer.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 10 (b) shows the phase jittering when the phase stabilization is switched on in FIG. 9.

FIG. 10 (c) shows the drift of interferometer over 1000 s, detected and compensated by the phase stabilization device shown in FIG. 9.

FIG. 12 (b) shows the near-field image taken at the same conditions of FIG. 12 (a) with phase stabilization function switched off.

DETAILED DESCRIPTION

Generally speaking, the embodiments described herein are directed to a method for obtaining absorption spectra from near-field infrared scattering using homodyne detection. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific method, structural and functional details disclosed herein are not to be interpreted as limiting but merely as a basis for the claims and as a representative basis for teaching one skilled in the art to variously employ the present invention. For purposes of teaching and not limitation, and a method for obtaining absorption spectra from near-field infrared scattering using homodyne detection is disclosed herein.

As used herein, the terms "about", and "approximately" when used in conjunction with ranges of concentrations, temperatures or other physical or chemical properties or characteristics is meant to cover slight variations that may exist in the upper and lower limits of the ranges of properties/characteristics.

As used herein, "homodyne detection" means a method of detecting amplitude and phase changed radiation field by mixing with a reference radiation from the same source and detecting the intensity change of the mixed field. In ANSOM, homodyne detection means mixing the light scattered by the tip-sample interface with a reference light field and detection by a square law light detector. The amplitude and phase of the reference light field can be controlled by attenuation and optical path delay. Homodyne detection also amplifies the optical signal, and improves the signal-to-noise ratio.

As used herein, "Apertureless near-field scanning optical microscopy (ANSOM)" refers to a microscopy method for investigation of nanostructures that overcomes the far field diffraction limit by scattering the evanescent waves at the near field of the sample with a sharp scanning probe tip. In various literatures, it is synonymous to scattering type scanning near-field microscopy (s-SNOM).

As used herein, "infrared nanospectroscopy" means a method that obtains infrared spectra reflecting infrared absorption profiles from nanometer-sized sample with a spatial resolution better than tens of nanometers.

As used herein, the phrase "nanoscale objects" means an object that has a dimension of interest that is smaller than one micrometer, and therefore cannot be spatially resolved by far-field spectroscopy due to the diffraction limit of near and mid infrared portions of the electromagnetic spectrum.

Figure 1:
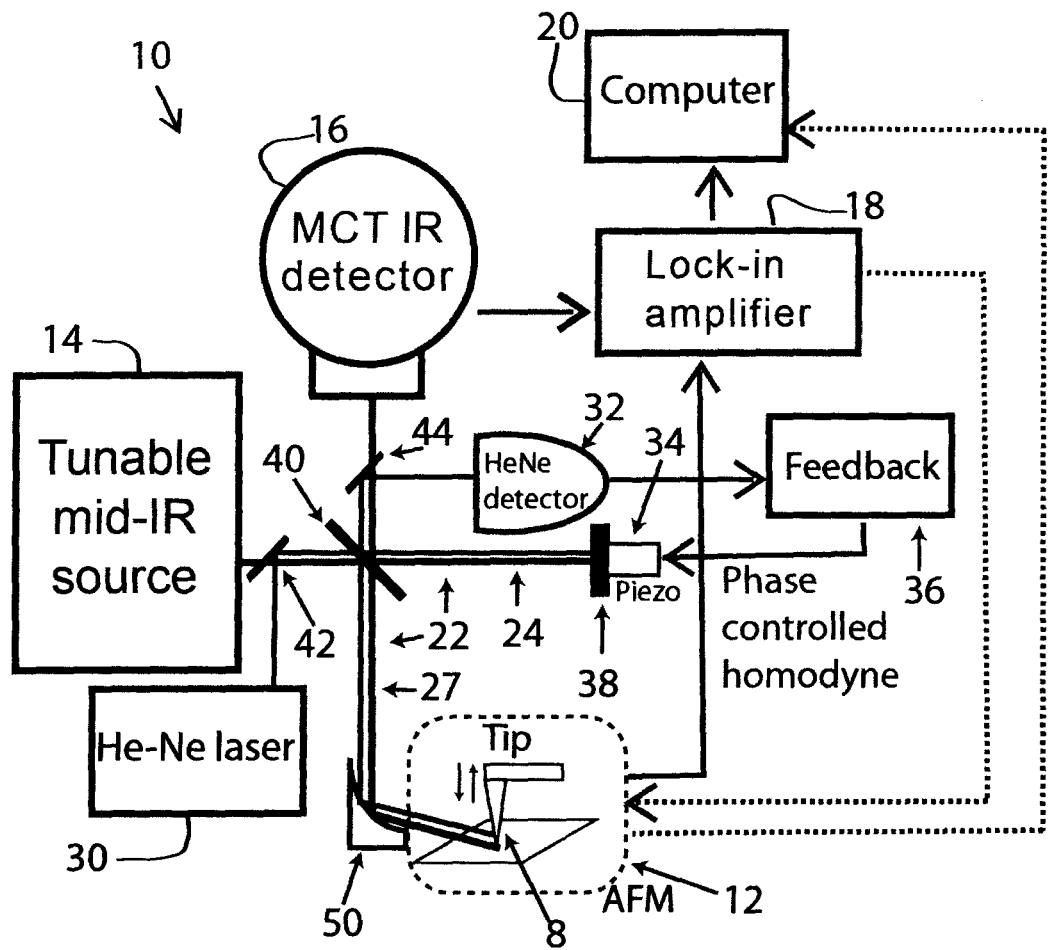
FIG. 1 illustrates a schematic of an apertureless near-field scanning optical microscopy (ANSOM) modified according to the present invention.

FIG. 1 shows a system for implementing the present method using an ANSOM apparatus shown generally at 10. System 10 includes two parts, the first being a typical interferometric ANSOM apparatus and the second being a precise phase control modification. The typical ANSOM apparatus includes a sample scanning atomic force microscope 12, a frequency tunable mid-infrared (IR) laser source 14, mercury cadmium telluride (MCT) IR detector 16, a lock-in amplifier 18, an auxiliary computer 20 and a Michelson interferometer 22 with reference arm 24 to achieve homodyne detection.

The interferometer 22 of system 10 which provides the precise phase control modification includes beam splitters 40, 42, 44 and reflecting mirror 50 (it will be appreciated that reflecting mirror 50 may be replaced by any focussing element such as a lens, as long as it focuses or concentrates the laser into one spot or location, in this case the AFM tip), a He—Ne laser 30, a He—Ne detector 32, a piezoelectric element and controller 34, and a feedback element which includes a controller 36 for adjusting a position of piezo stage. The piezo-stage and controller 36 is for precisely controlling the displacement of mirror 38 in the reference arm 24 homodyne phase adjustment. In addition to typical ANSOM implementation, the system can also contain an optical path stabilization feedback mechanism based on optical interference of He—Ne laser reflections to prevent drift of the homodyne phase. It will be appreciated that the He—Ne laser for the feedback circuit to be discussed herebelow may be replaced by lasers of other wavelengths, however He—Ne lasers are preferred because they are readily available and economic. The same applies to the He—Ne detector. It will also be noted that while controller 36 is shown as a separate controller, (computer or microprocessor based controllers), it will be appreciated that computer 20 may be programmed with instructions/algorithms to provide the necessary feedback to the piezo stage 34. There is no requirement that the feedback controller 36 be a separate computer controller from computer 20.

It will be appreciated that, in addition to being a full reflector, mirror 38 instead may be a partial reflector which can be used to attenuate the reference light beam to a suitable intensity range without the use of a variable attenuator for the IR light field.

The atomic force microscope 12 provides functionality to raster scan a sample underneath scanning probe tip with nanometer precision, maintaining a close tip-sample distance while tip is mechanically oscillating. The mid-IR laser source 14 provides tunable radiation to cover the infrared absorption band of the sample. It will be noted that the light source 14 is a frequency tunable coherent light source which may emit a continuous beam of coherent light or it may be a pulsed coherent light source.

The MCT IR detector 16 converts infrared radiation into a voltage signal which is fed into the lock-in amplifier 18 as shown in FIG. 1. The lock-in amplifier 18 demodulates the voltage fluctuations at the mechanical oscillation frequency of the tip, and frequency harmonics. This is achieved by AFM 12 being connected to the lock-in amplifier 18 shown in FIG. 1. The lock-in amplifier 18, based on the input from the AFM 12 and the MCT detector 16, demodulates the MCT voltage signals into harmonics (first, second and third etc.) of the AFM tip 8 oscillation frequency.

The computer 20, connected to lock-in amplifier 18, records the lock-in demodulation signal as the sample is scanning underneath the AFM tip 8 to form an ANSOM image based on the absorption of the sample under the $\pi/2$ homodyne condition and visually displays the spectroscopic mapping on the computer image display. The absorption spectrum is constructed by extraction of lock-in signals taken at the same location with incremental IR frequencies from multiple ANSOM image scans with the $\pi/2$ homodyne condition which can then be displayed on the image display.

Computer 20 may be part of the atomic force microscope 12 or it may be a stand-alone computer and in any case it is programmed with instructions such that the second and higher harmonic components from the lock-in 18 it forms near-field scanning optical microscope image(s) of the nanoscale objects and to display the image(s) on the image display.

FIG. 1 shows the output of the AFM 12 going to the lock-in 18 and the output (second and higher harmonics) from the lock-in 18 go to the computer controller 20. Alternatively, the output of the lock-in 18 (second and higher harmonics) may go to the AFM 12, and then AFM 12 is programmed to provide information to the computer 20. Both options are performing the same functions.

Instead of using a physical lock-in amplifier, it will be understood that its function may be replaced using a "software" based lock-in amplifier in a computer. In this case, the soft-ware based lock-in uses waveform digitization with a high speed A/D (analog to digital converter) and Fourier transform analysis to give the same result as the physical lock-in 18. It will be understood that the lock-in functionality can be replaced by a set of A/D converters and field programmable gate array (FPGA) processors to perform either lock-in or alternative analysis to extract near field absorption signals.

The Michelson interferometer 22 containing reference arm 24 and sample/tip arm 27 is used to detect the amplitude and phase changes between the tip scattered light and the reference light. The reference arm 24 has a computer controlled piezo stage 34 to precisely change the optical path of the reference arm to achieve the $\pi/2$ homodyne condition discussed below.

An embodiment of the feedback device may be an optically-based feedback device. In this embodiment, an optical part of the feedback system includes a coherent light source 30 having a wavelength shorter than that of the IR light source 14. This gives better sensitivity and detectability using the reference arm. An embodiment includes a He—Ne laser 30, a He—Ne detector 32 and various beam splitters 40, 42, 44. A small beam diameter 632.8 nm He—Ne laser beam propagates in the same direction as the mid-IR beam to the probe tip area, impinges upon the cantilever portion (not shown) of the scanning probe tip 8 and is reflected back. Similarly, part of the He—Ne laser beam goes through beam splitter 40 and is reflected by the reference mirror 38, is recombined using the beam splitter 40 and is separated from the mid IR light beam and is detected by the He—Ne detector 32. The interference between cantilever-scattered fields and the He—Ne light field reflected in the reference arm 24 reveals the optical path drift between the two interferometer arms 24 and 27. A computer-controlled feedback unit 36 is used to maintain the intensity by shifting the piezo stage 34 locations at suitable time intervals to recover the interference contrast of the He—Ne light.

While the above feedback control system is an optical based feedback system to maintain the optical phase difference discussed above, it will be appreciated that other feedback systems may be used.

In a non-limiting embodiment, computer-controlled feedback unit 36 includes a computer, A/D card and a computer program to read the signal value from the He—Ne detector 32 at the $\pi/2$ condition for the IR light and maintain the same signal value during the sample scanning by adjusting the voltage of the piezo stage 34. In general, feedback can be done in many ways, as will be appreciated by those skilled in the art, with the goal of it being to stabilize the optical phase difference $\phi$ of the interferometer 22.

It will be appreciated that the coherent light source may be a broadband infrared light source, and includes a frequency selection device located either at an output of said broadband infrared light source configured to select a specified frequency of light to be passed into the interferometer, or located at the input of the detector configured to select a specified frequency of light to be passed into the detector. The frequency selection device may simply be filter or it may be a Fourier Transform interferometer.

The coherent light source may be a frequency tunable narrow band coherent light source.

In operation, a laser beam produced by the frequency tunable laser light source 14 passes through/reflects from the 50:50 IR beam splitter 40. The reflected half of the IR light beam is reflected onto the sample by an achromatic focusing element such as the off-axis parabolic mirror 50 and focussed on the apex of an oscillating atomic force microscope tip 8 that is weakly interacting with the surface. The scattered IR light is collected and directed by the same focusing element 50 onto the MCT IR detector 16. The other half of the IR light beam which passes through beam splitter 40 is then retro-reflected by mirror 38 mounted on the piezo stage 34 for homodyne phase adjustment. The retro-reflected light and scattered IR light are recombined by the same IR beam splitter 40 and detected by the MCT IR detector 16 with an appropriate preamplifier. The voltage signal from the MCT detector 16 is coupled into lock-in amplifier 18 to be demodulated at second or higher harmonics of the tip oscillation frequency. An ANSOM image is recorded when scanning the tip 8 location over a nanoscale object. The relevant $\phi=\pi/2$ homodyne condition is achieved by minimizing the lock-in demodulation signal at second or higher harmonic over a known non-resonant region of the sample, such as a gold coated substrate.

The relevant $\phi=\pi/2$ homodyne condition may also achieved manually by precisely matching the optical path length of the two interferometer arms 24 and 27 of the interferometer 22, and then offset the length of the interferometer arm 24 by the distance of one eighth of the laser wavelength of the IR source 14.

In other words the relative phase difference includes an absolute optical phase difference between the light beams in the reference arm and the sample arm, measured by an optical path length difference between the reference arm and the sample arm and divided by a wavelength of the coherent light source, and multiplied by $2\pi$.

The $\phi=\pi/2$ (or $-0.5\pi$) homodyne condition is maintained by a mechanically rigid instrument as well as a He—Ne optical path feedback. Note that the auxiliary feedback laser 30 can in principle be any visible laser and is not restricted to a He—Ne laser.

Figure 2:
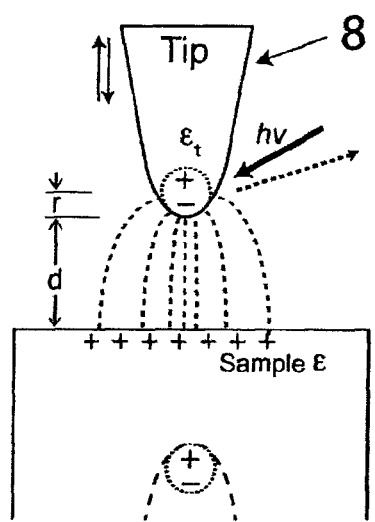
FIG. 2 shows an image dipole model of a tip sample.

Referring to FIG. 2, ANSOM uses a sharp metallic scanning probe tip 8. Under the illumination of the light field, the sharp tip generates charge polarization according to its polarizability at the frequency of the light. Such a charge polarization induces charge redistributions in the measured sample, leads to an overall tip-sample polarizability. In this example, an image dipole approximation was used to describe such interaction, but other approximations are possible.

The polarizability of the metallic tip 22 as a dipole is described by $$\alpha = \frac{4\pi^3(\varepsilon_t - 1)}{\varepsilon_t + 2}$$

with $\varepsilon_t$ being the dielectric function of the metallic tip 22. The total polarizability of tip and sample is then expressed as:

$$\alpha_{eff} = \left(\alpha - \frac{\alpha\beta}{16\pi(r+d)^3}\right)^{-1} \quad (1)$$

with r and d being the tip radius and distance to the sample. $\beta$ is defined as $\beta=(\varepsilon-1)/(\varepsilon+1)$ with $\varepsilon$ being the dielectric function of the sample. Equation (1) allows numeric simulation of near-field scattering as a function of tip sample distance, light frequencies, and dielectric functions of sample and tip material.

Figure 3:
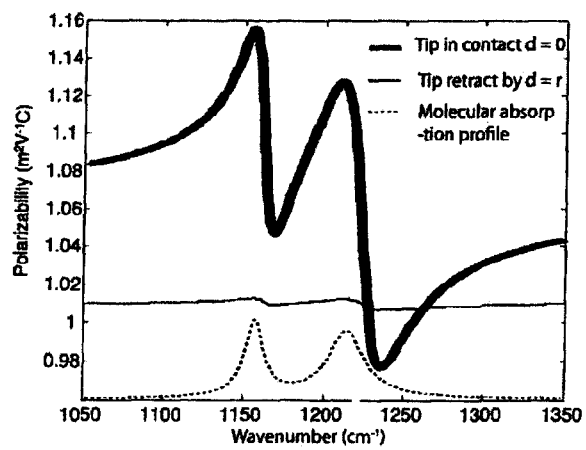
FIG. 3 shows numeric simulation of a tip sample polarizability of two conditions, the first being the tip in contact with sample (thick curve), and in the second the tip being separated from the surface by one radius (thin curve). The extinction coefficient of the sample (absorption profile) is shown for reference (dashed line).

FIG. 3 shows a plot of a simulation of the amplitude of effective polarizability when the tip is just in contact of the sample (thick curve) and retracted by one tip radius (thin curve). The spectrum of the effective polarizability assumes a dispersive profile in contrast with the molecular absorption profile shown as thin dashed curve. The simulation is based on spectroscopic data obtained from far-field measurements of poly(tetrafluoroethylene) (PTFE), The detection of light scattered from tip 8 and the sample is done interferometrically. A reference optical field with properly controlled phase is mixed with the scattered optical to produce homodyne amplification. The mathematical expression for such homodyne procedure is shown as $I_{total}=1/4|\alpha_{eff}E+Ae^{i\phi}E|^2$ which is $$I_{total}=1/4|E|^2((re\{\alpha_{eff}\}+A\cos\phi)^2+(im\{\alpha_{eff}\}+A\sin\phi)^2) \quad (2)$$

A is the amplitude of the light coming from the reference arm 24 reflected off the mirror 38, and directed onto the MCT IR detector 16. E is the amplitude of the incident light from the IR source 14, assuming no losses. The angle $\phi$ is the optical phase difference between the light beams in the two arms 24 and 27 of the interferometer 22.

It is noted that the amplitude A in arm 24 and the phase difference $\phi$ between the reference and sample beam scattered from the tip 8 are controlled using optical attenuation and a variable path delay using piezo stage 34. In the method disclosed herein, by selecting or setting the value of $\phi$ equal to $\pi/2$, the contribution from the imaginary part of the effective polarizability is maximized ($\sin(\pi/2)$ is equal to 1}, and at the same time the contribution from the real part of the polarizability is minimized { $\cos((\pi/2)$ is zero}. This also allows the setting the experimental condition of $\pi/2$ by minimizing the scattering from the non-resonant locations of the sample, such as a substrate.

It will be understood that while setting φ equal to π/2 gives the best result in terms of minimizing the contribution of the real part of the polarizability and maximizing the contribution of the imaginary part of the polarizability, the present method will work at phase differences around n/2, even though it would not give the same best results at π/2. Setting φ equal to a value between 0.4π to 0.6π (or −0.4π to −0.6π) is contemplated by the inventors to work, albeit not as well as setting φ equal to a value of 0.5π, (or −0.4π) which, as shown in equation (2) gives the maximum benefit in terms of maximizing the contribution from the imaginary part of the effective polarizability while at the same time minimizing the real part of the effective polarizability.

Figure 4:
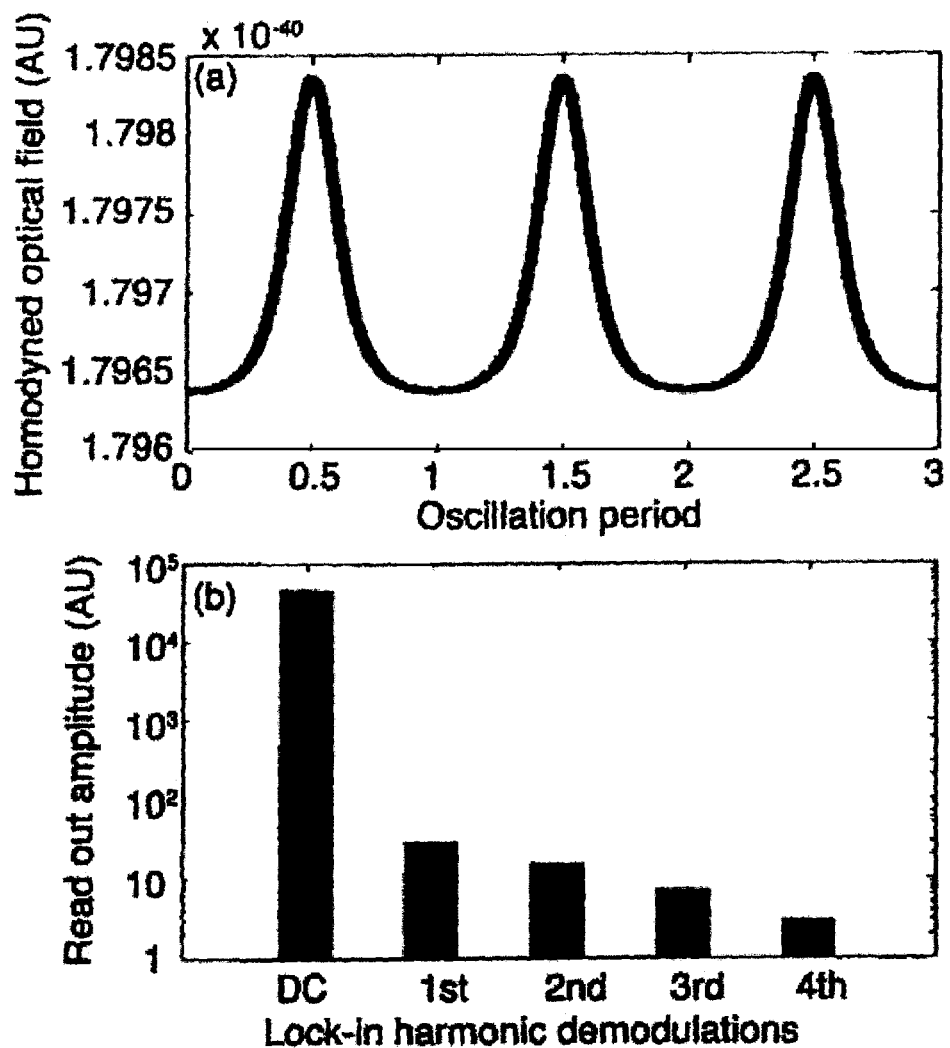
FIG. 4(a) shows the detectable optical signal waveform as a function of tip oscillation period.
FIG. 4(b) shows the corresponding Fourier analysis of the waveform of FIG. 4(a) which gives multiple harmonics at the tip oscillation frequency.

One can simulate the homodyne-detected waveform with $I_{total}$ vs. time by assuming a periodical oscillation of the vertical position of scanning probe tip in intermittent contact operation. An illustrative plot of tip-sample effective polarizability vs. tip oscillation is shown in FIG. 4(a). Corresponding lock-in demodulations are shown in FIG. 4(b). The anharmonic components from the tip sample polarizability are extracted from the non-fundamental harmonics ($n>=2^{nd}$), which provides discrimination between far-field and near-field signal in the measurement. The extracted second harmonic component is used in following simulation figures.

Figure 5:
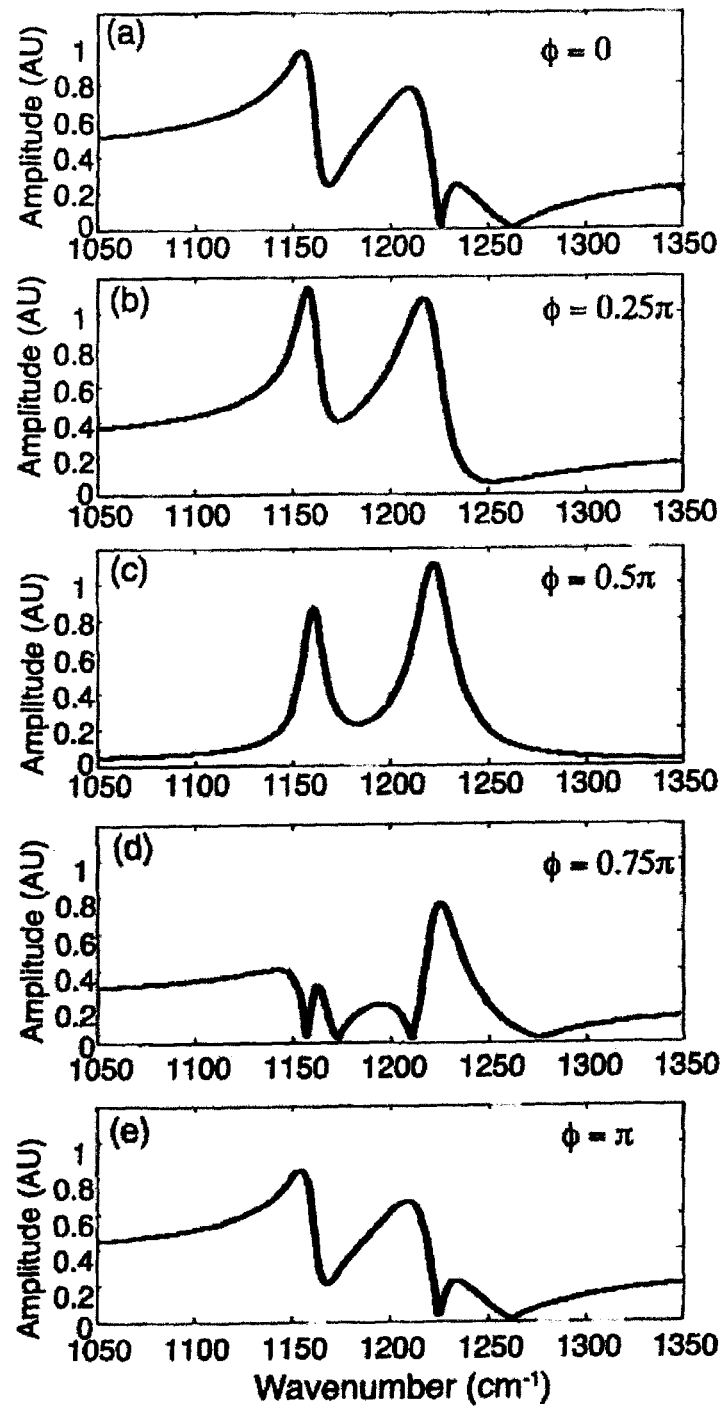
FIGS. 5(a) to 5(e) show second harmonic lock-in read out profiles under different reference phase values from 0 to $\pi$, the phase value being shown in the top right hand corner of each profile.

One can proceed with this numeric simulation with controlled reference phase. A comparison of homodyne detected lock-in second harmonic demodulation with φ value between 0 and π with increment of π/4 in FIG. 5(a-e), with reference field amplitude A equals to 10 times the tip-sample scattered light. It is clear that when the reference phase is set at φ=0.5π the lock-in detected signal gives absorptive profile (FIG. 5(c)), whereas the other phase value gives dispersive profile or a combination of dispersive profiles with lock-in features.

Figure 6:
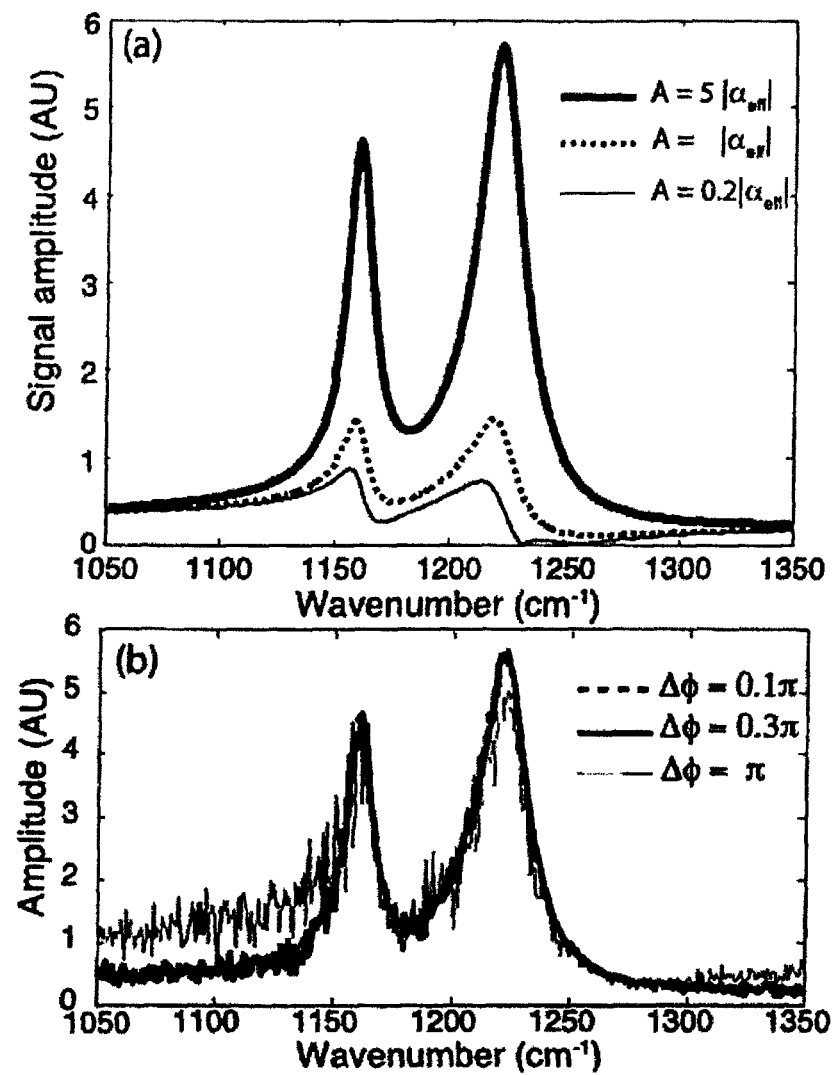
FIG. 6(a) shows the effect of reference amplitude on the lock-in read out.
FIG. 6(b) shows the effect of phase noise on the lock-in read out.

The condition for obtaining the absorption profile directly from lock-in demodulation of the detected signal not only requires φ=0.5π but also a reference amplitude A sufficiently larger than that of the near-field scattered optical field. One can investigate with numeric simulations, the effect of A with three different values: 20%, 100%, and 500% of the amplitude of near-field scattering, while the phase is fixed at φ=0.5π. The results are shown in FIG. 6a. In this way one can estimate that the threshold value for A is about 5 times of the amplitude of near-field scattering. Below this threshold, the lock-in readout will have dispersive profiles even with phase being set correctly.

Evaluation of the response to noise is necessary to demonstrate the robustness of the proposed procedure of π/2 phased homodyne in ANSOM. One can add value-controlled noise into the numerical model and find a threshold value for phase stability in this procedure. The results are shown in FIG. 6b. It is estimated that the threshold for phase noise is 0.3π that corresponds to about 0.9 μm of optical path at 6 μm wavelength. If one considers a double pass of light within optical reference arm 24, the arm requires path length stability of only about 450 nm, which is attainable with a rigid and stable mechanical design of the interferometer 22.

The feedback mechanism 36 based on maintaining interferometric contrast by employing a short wavelength He—Ne laser shown in FIG. 1 enables one to surpass this stability requirement of the homodyne phase and deliver high quality absorption spectra from a nanoscale sampling area.

Figure 7:
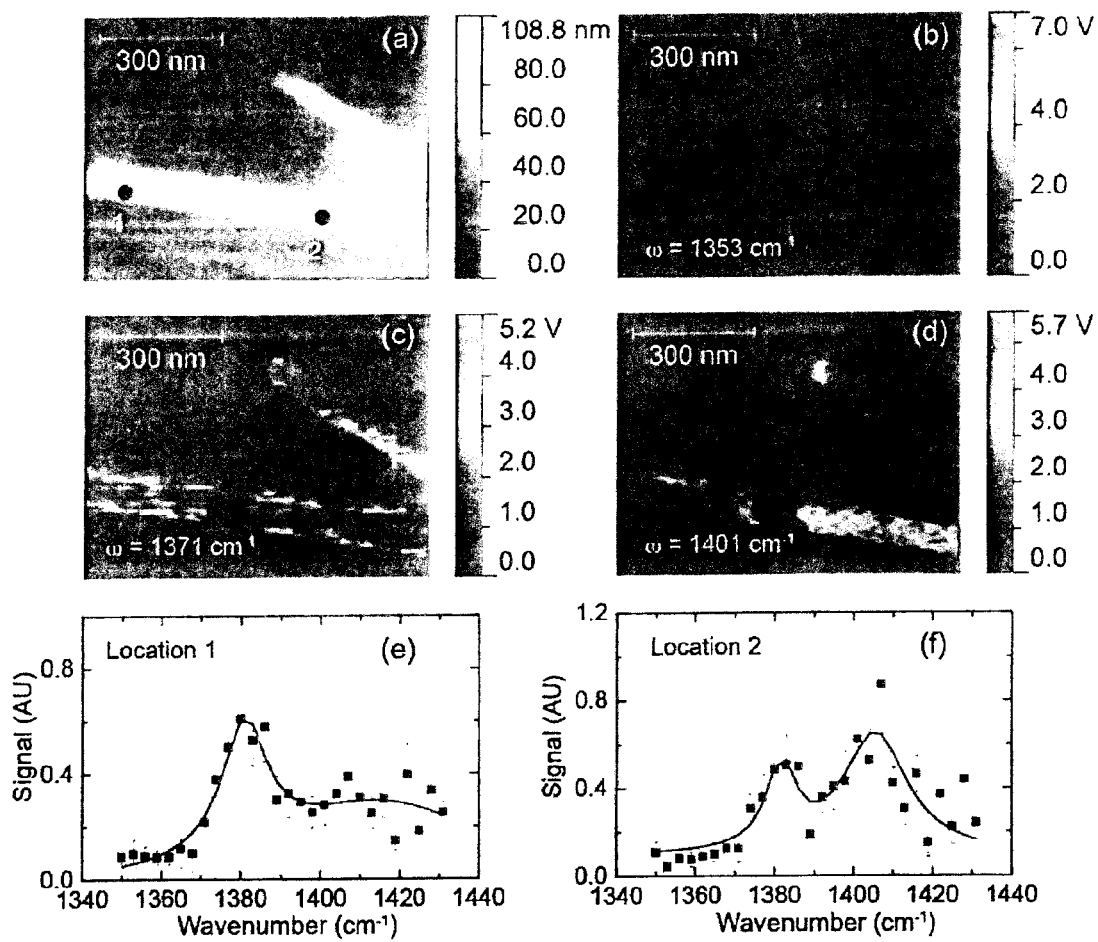
FIG. 7(a) shows the topography of boron nitride nanotubes (BNNTs) obtained with tapping mode AFM during ANSOM scan.
FIG. 7(b) shows the ANSOM image collected under the $\pi/2$ homodyne condition with mid IR light source tuned off resonance with this sample (boron nitride nanotube (1353 $cm^{-1}$)).
FIG. 7(c) shows the ANSOM image with laser source tuned on the resonance with BNNT tube (1371 $cm^{-1}$).
FIG. 7(d) shows the ANSOM image with laser source tuned to a weak resonance band with this BNNT tube (1401 $cm^{-1}$).
FIG. 7(e) shows the reconstructed spectrum from normalized scattering intensity (ANSOM voltage divided by laser power) of the location specified on FIG. 7(a) as point 1.
FIG. 7(f) shows the reconstructed spectrum from normalized scattering intensity (ANSOM voltage divided by laser power) of the location specified on FIG. 7(a) as point 2.

The inventors have experimentally implemented the invention of the π/2 phased homodyne method for ANSOM and tested it on Boron Nitride nanotubes on gold substrate in a region less than one micron by one micron in area. Vibrationally sensitive images and near field absorption spectra have been obtained. FIG. 7a shows the topography obtained with intermittent contact mode AFM during ANSOM scan. FIG. 7b shows the ANSOM image collected under the π/2 homodyne condition with the mid IR source tuned off resonance for this tube (1353 $cm^{-1}$). FIG. 7c shows the ANSOM image with laser source tuned on resonance with the BN nanotubes (1371 $cm^{-1}$). When the laser is tuned onto the resonance of sample, with π/2 phase homodyne condition, the scattered light increases significantly from the BNNT tube while the scattering from gold substrate remains low. FIG. 7d shows the ANSOM image with the laser source tuned to the resonance band of BNNT tubes (1401 $cm^{-1}$) where it is strongly resonant for the lower right side of BN tube and the terminal end of upper tube.

The frequency dependence of scattering intensity under the π/2 homodyne condition allows reconstruction of the absorption spectrum from multiple chemical sensitive imaging scans. FIGS. 7e and 7f shows the reconstructed spectrum from normalized scattering intensity (ANSOM voltage divided by laser power) of this location 1 and 2 on BNNT (marked in FIG. 7a). Lorentzian fits (shown in FIGS. 7e and 7f) are added to uncover the positions and widths of vibrational resonances from two locations, revealing the composition variations even within one nanotube. The experimental results of ANSOM collected under the π/2 homodyne condition have demonstrated vibrationally sensitive imaging and infrared nanospectroscopy of individual objects of nanometer dimensions.

One embodiment of the phase feedback is to use the far-field scattered light by the cantilever region of the scanning probe tip and feedback on that scattered light's phase relative to the light in the reference arm. A small amplitude D (less than 40 nm) modulation at frequency F (typically 500 Hz) is applied to the reference mirror with its central position set around the π/2 phase position described by above mentioned procedure. A two-channel fast data card acquisition card is used to acquire the detected signal from the detector and the modulation waveform in voltage. A computer is used to perform lock-in detection on the signal with the modulation frequency at the reference frequency of the lock-in detection. The first and second harmonic demodulation outputs from the lock-in detection are recorded with both amplitude and phase, giving amplitude of the first and the second harmonic $A_1$, $A_2$ and lock-in phase of the first and second $φ_1$, $φ_2$. A magnification ratio is calculated using $R_{21}=J_1(4πD/λ)/J_2(4πD/λ,)$. $J_1$ and $J_2$ are the Bessel function of the first kind. A waveform W(t) is synthesized with amplitude with formula $W(t)=A_1 \sin(F\ t+φ_1)+R_{21}A_2 \sin(F\ t+φ_2)$. Then, the waveform is processed by the computer processor in a fast Fourier transform routine to obtain the phase value $φ_F$ at the frequency F. The value $φ_F$ corresponds to the relative phase difference between the reference light and the light scattered from the cantilever portion of scanning probe. A feedback loop is used to lock the value of $φ_F$ by offsetting the piezo-stage against possible drift or long term fluctuations. This implementation results in an improvement of the vibrational sensitive imaging quality.

Figure 8:
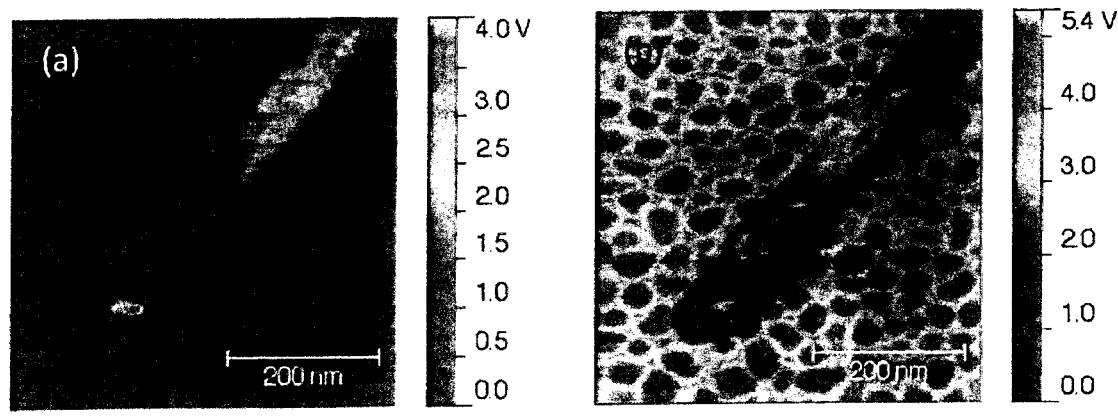
FIG. 8(a) shows a vibrational sensitive image of a BNNT with implementation of stabilization phase feedback lock at $\pi/2$ homodyne phase.
FIG. 8(b) shows the vibrational sensitive image of a BNNT with implementation of stabilization phase feedback lock at zero homodyne phase.

We have obtained better quality vibrational sensitive near-field images with this phase feedback mechanism. FIG. 8a shows a vibrational sensitive near-field image of BNNT at 1390 $cm^{-1}$ of 500 nm region with π/2 phase. FIG. 8b shows an in-phase image under otherwise identical configuration. The imaging quality is considerably improved in this case, compared with what is seen in FIG. 7b-d.

Another embodiment of the phase feedback is to use an auxiliary laser in the same interferometer of the infrared laser in the near-field microscope and feedback the optical path of the interferometer. The optical interference of the auxiliary laser between two interferometer arms is detected; the difference between phase fronts of auxiliary laser in the interferometer arms are calculated and used to provide a feedback. The feedback device maintains a constant wave front phase difference for the auxiliary laser.

Figure 9:
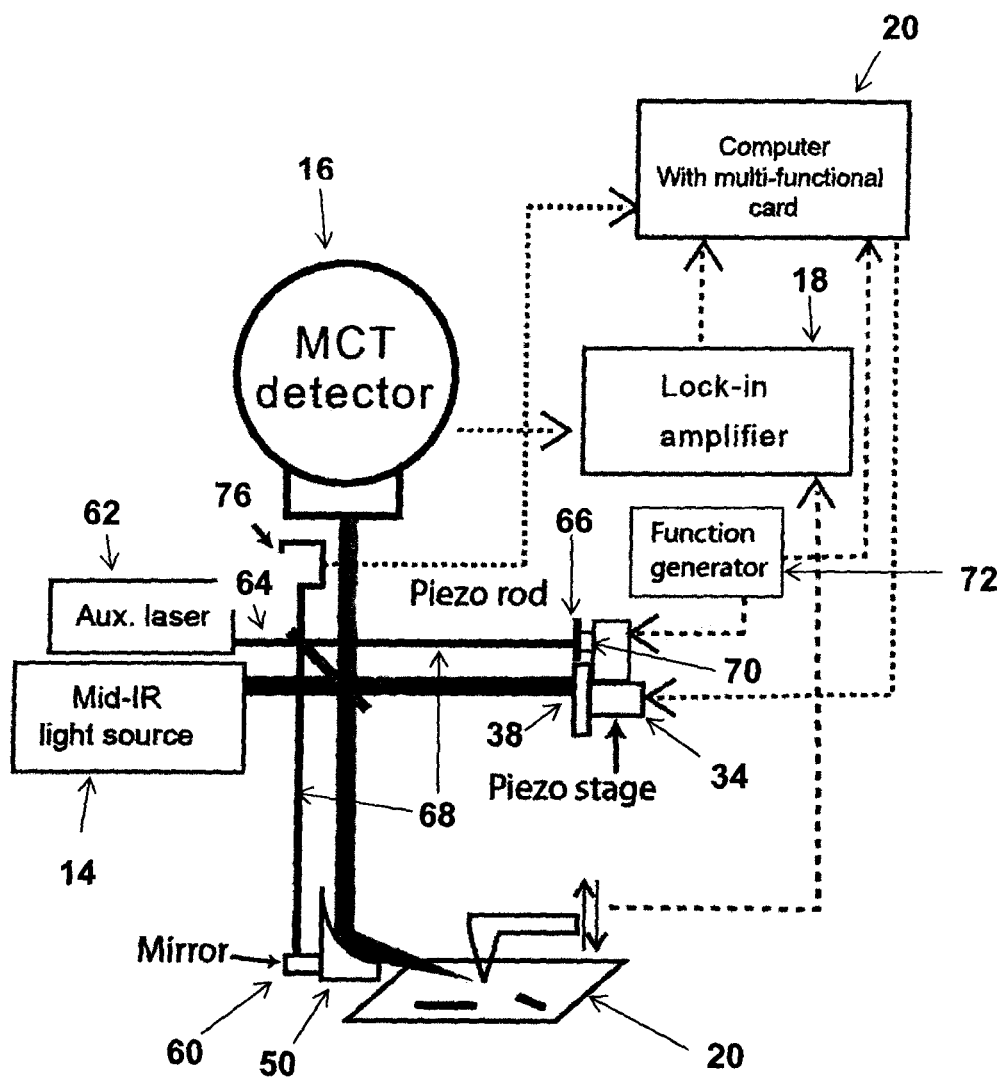
FIG. 9 shows the scheme of an embodiment of the apparatus with auxiliary phase stabilization.
Figure 9A:
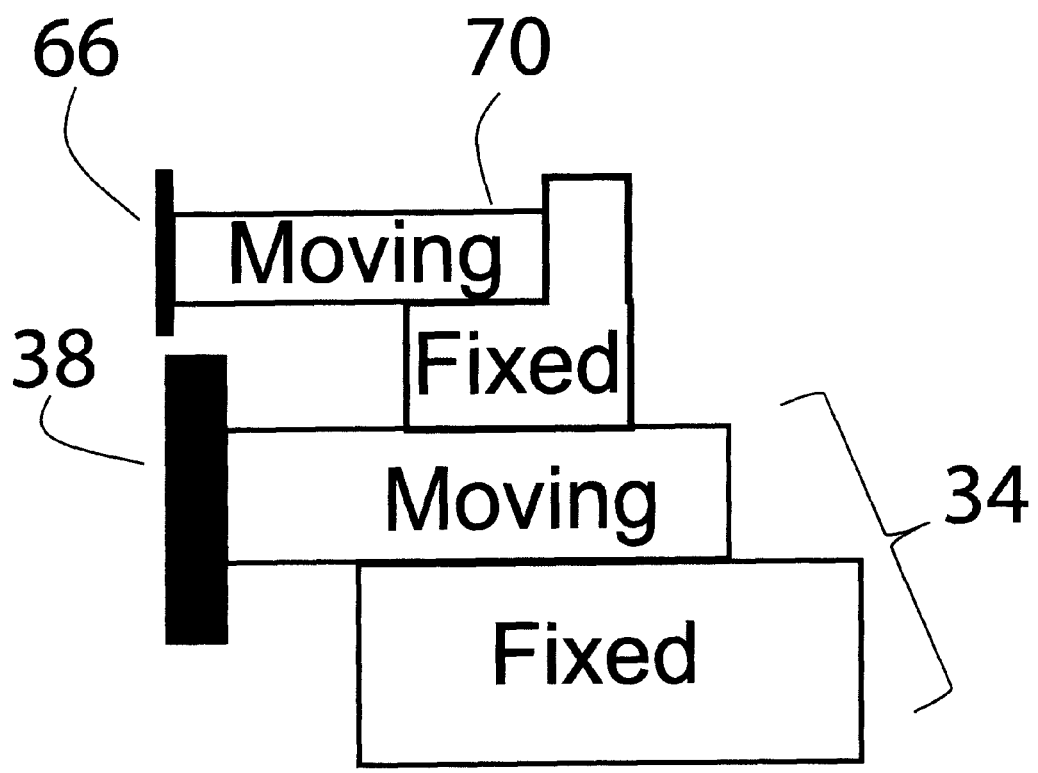
FIG. 9a is a side view of a positioning mechanism for positioning a reflector in a reference arm of an interferometer forming part of the apparatus of FIG. 9.

FIG. 9 shows the scheme of this embodiment. A flat mirror 60 is mounted on the focusing parabolic mirror 50 of the infrared laser 14. A laser beam 64 emitted by auxiliary laser 62 is split into two beams through the same beam splitter 40 as the infrared laser from laser 14. One part of the auxiliary laser beam 64 is reflected from the additional mirror 60 mounted on the parabolic mirror 50. The other part is reflected on a mirror 66 mounted on a piezo rod 70. The piezo rod 70 is fixed on the larger piezo stage 34 where the reference mirror 38 for the infrared light is mounted. A function generator 72 generates a sinusoidal voltage waveform to drive the piezo rod 70 at a frequency f (a few hundred Hz) with an oscillation amplitude D of ~100 nm. Auxiliary laser of wavelength $\lambda$ from laser 62 (e.g. HeNe, or a diode laser) is guided into the interferometer 22 and reflected by the mirror 66 on the piezo rod 70 to from a Michelson interferometer. FIG. 9a is a side view of a positioning mechanism for positioning a reflector in the reference arm of the interferometer. One end of the piezo rod 70 is tethered to the moving part of piezo stage 34. The other end of the piezo rod 70 is used to mount mirror 66. The sinusoidal voltage waveform from the function generator 72 causes the piezo rod 70 to expand and shrink, therefore driving the position of the mirror 66 back and forth in a sinusoidal motion. The mirror 38 is mounted on the moving part of the piezo stage 34. The fixed part of the piezo stage 34 is fixed with respect to the rest of the instrument. The position of the moving part of the piezo stage 34 is adjustable either with an external applied voltage from the multifunctional card in computer 20, or a user accessible knob.

A photodiode 76 is used to read out the optical signal of the auxiliary laser 62 out of the Michelson interferometer. The voltage signal from the photodiode 76 is transmitted to computer 20 which is equipped with a multifunctional card. The multifunction card is programmed with algorithms/instructions to perform lock-in detection on the auxiliary laser signal with the input of the reference frequency set to the sinusoidal frequency of the functional generator 72. The amplitudes of the first harmonic (f) and the second harmonic (2f) of the lock-in detection by the multifunctional card on the signal from the photodiode 76 are read out as $A_1$ and $A_2$.

The phases of the first and second harmonic of the lock-in detection by the multifunctional card are read out as $\phi_1$ and $\phi_2$. The phase read out from lock-in are between $-\pi$ and $\pi$. An algorithm is used to convert $A_1$, $A_2$ and $\phi_1$, $\phi_2$ into the phase difference of the auxiliary laser beam in the interferometer 22. The algorithm used in this embodiment is described as follows: A magnification ratio $R_{21}$ is calculated as $R_{21}=J_1(4\pi D/\lambda)/J_2(4\pi D/\lambda)$. $J_1$ and $J_2$ are the Bessel function of the first kind. The signs of the phase angles from the first lock-in harmonic and the second lock-in harmonic are calculated as $S_1=\text{sign}(\phi_1)$ and $S_2=\text{sign}(\phi_2)$ i.e., if the phase angle is positive, $S=1$, if the phase angle is negative $S=-1$.

The phase difference of the auxiliary laser beam in the interferometer 22 is calculated as $$\Delta\phi = \operatorname{atan}\left(S_1 R_{21} \frac{A_1}{A_2}\right) + 0.5\pi \text{ if } S_2 = 1,$$

$$\text{and } \Delta\phi = \operatorname{atan}\left(-S_1 R_{21} \frac{A_2}{A_1}\right) + 1.5\pi \text{ if } S_2 = -1.$$

The read out of the phase difference of the auxiliary laser beams in the interferometer 22 gives a value between 0 and $2\pi$. A $\pi/2$ homodyne condition of the infrared laser from infrared laser source 14 is set by procedures described above through adjusting the position of piezo stage 34. Such a condition gives a phase difference of the auxiliary laser beam $\Delta\phi_0$ that is used as a set point for the phase feedback. A software PID loop by the computer 20 is used to minimize the read out phase difference $\Delta\phi$ and set point $\Delta\phi_0$ by adjusting the voltage applied on the piezo stage 34 of the infrared laser provided by the multi-functional card in the computer 20.

Figure 10:
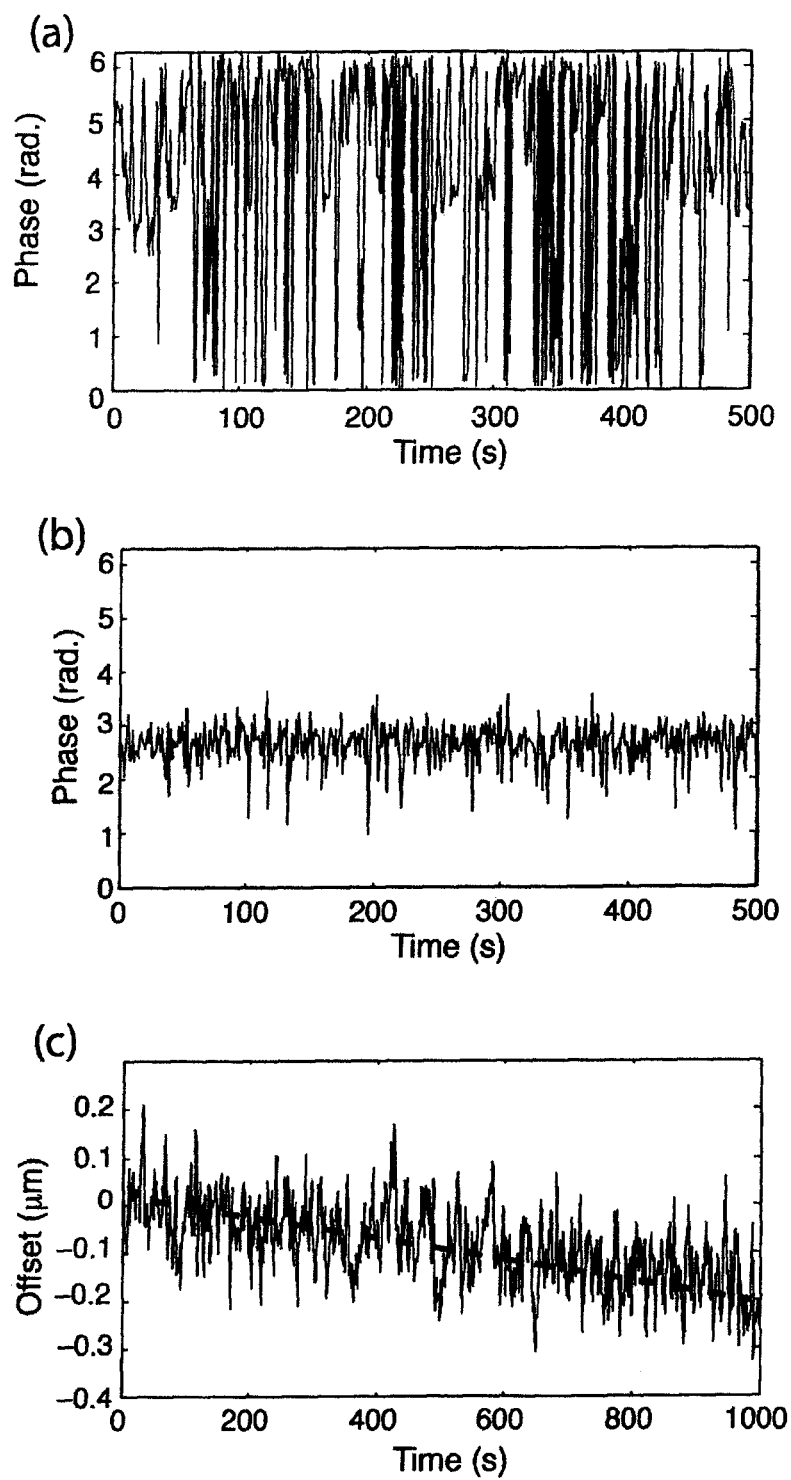
FIG. 10 (a) shows the phase jittering when the phase stabilization is switched off in FIG. 9.

The wave front phase difference of the auxiliary laser 62 in the interferometer 22 is stabilized to $\Delta\phi_0$, which means that the optical path difference between two interferometer arms are maintained at the optical path difference that satisfies the $\pi/2$ homodyne condition of the infrared light. FIG. 10a shows the detected phase with and without the phase feedback device. A stabilization of phase to a rms. less than 1 rad is found. For the infrared laser, this stabilization corresponds to less than 0.1 rad deviation from the phase set point. The phase feedback mechanism is capable of offsetting the long term drift. FIG. 10b shows the drift compensation during 1000 s time period. A drift of 200 nm is detected and simultaneously compensated.

Figure 11:
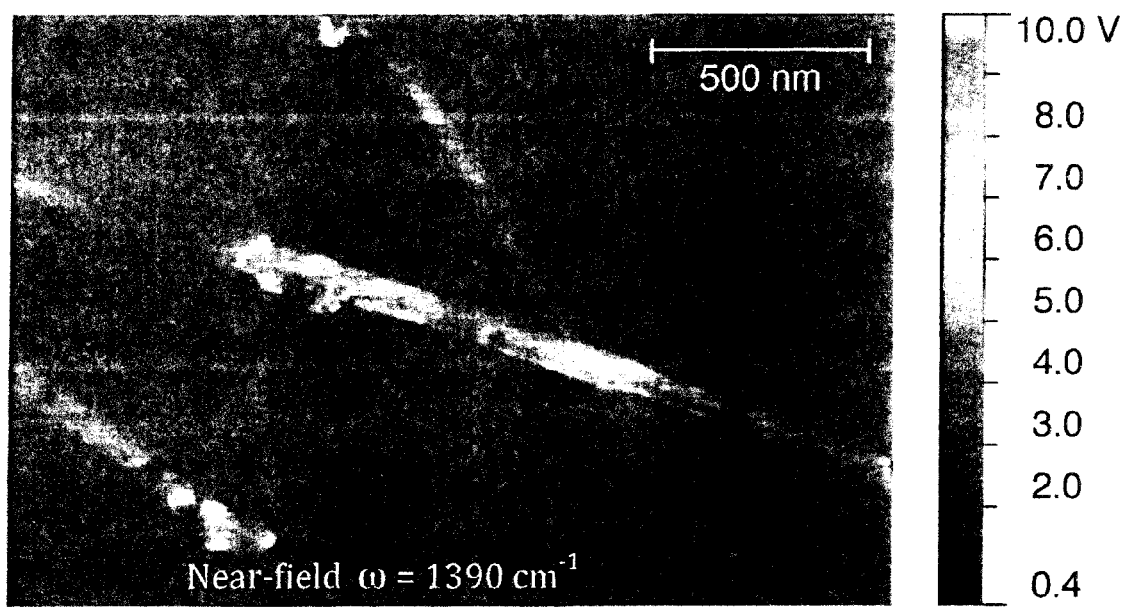
FIG. 11 shows the near-field image of two crossing BNNTs with this embodiment of the instrument shown in FIG. 9.

Such a stabilization of the interferometer phase increases robustness against mechanical fluctuation, air turbulence, or thermal expansion of the instrument and platform that supports the instrument. It allows a less than 0.1 rad phase jittering at the infrared frequency. The separation between feedback mirror and the infrared reference mirror allows the phase of the infrared homodyne field be held at a stable value, without moving it back and forth of the reference mirror, therefore improving the accuracy of the phase homodyne detection even further than initial embodiment. FIG. 11 shows the near-field image of two crossing BNNTs taken at frequency 1390 cm$^{-1}$ with $\pi/2$ homodyne condition with this embodiment of the instrument.

The use of this phase stabilization mechanism to maintain the interferometer phase difference to specific multiple values of a fixed interval, such as 0, 0.5$\pi$, or $\pi$, which can be used to facilitate the extraction of infrared absorptive profiles by normalizations or calculation. A look-up table for multiple frequencies of said coherent tunable light source 14 can be created. Such a look-up table relates suitable positions of the piezo stage 34 with multiple wavelength of the laser, allowing a repeatable switching between laser wavelengths during ANSOM imaging with different infrared frequencies.

The use of the phase controlled homodyne method can be used with a broadband infrared light source, where the near-field response of each frequency is obtained through a frequency selector such as a monochromator or an infrared band pass filter. either by a physical filter or through a Fourier transform afterward.

Figure 12:
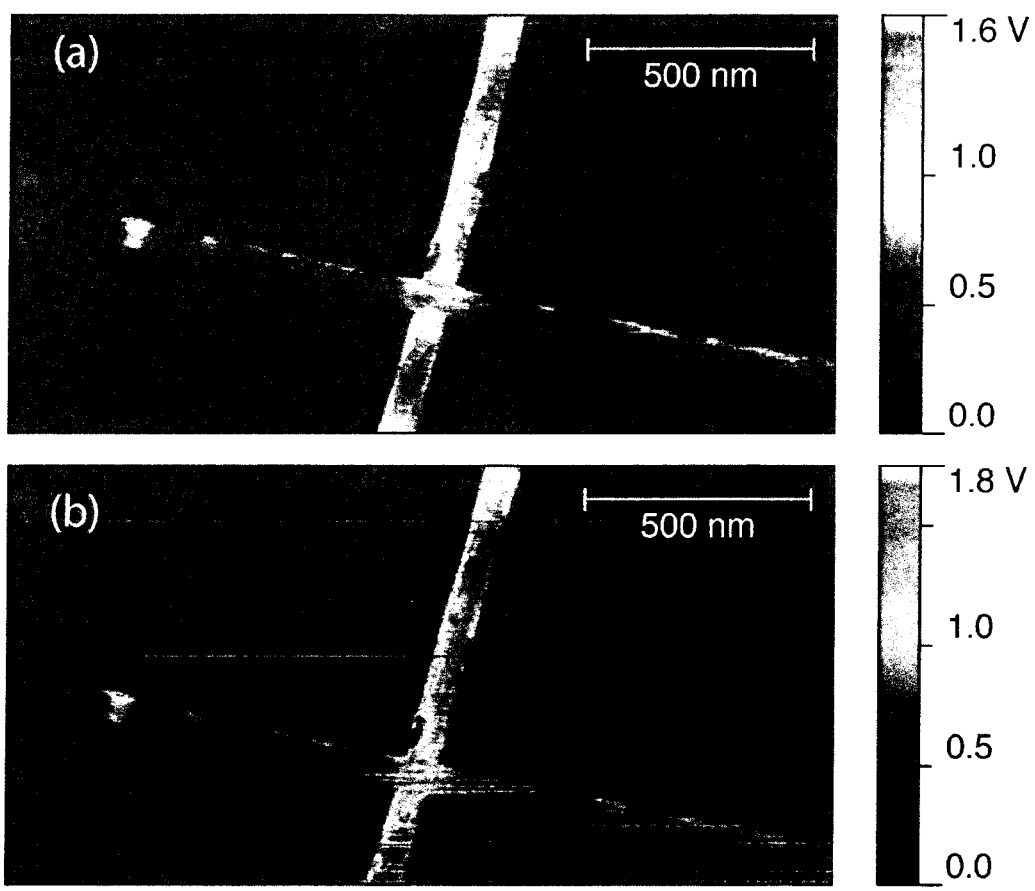
FIG. 12 (a) shows the near-field image taken at infrared frequency 1390 $cm^{-1}$ of two crossing BNNTs with phase stabilization function of the instrument shown in FIG. 9.

Thus, with respect to the embodiment of FIG. 9, the method includes using an auxiliary interferometer 68 located spatially adjacent to interferometer 22 formed by auxiliary laser 62, aligned parallel to the coherent light source 14, detector 76, reflector 60 in a fixed position with respect to the focusing element 50, additional reflector 66 which is affixed to positioning mechanism 70 which in turn is tethered to positioning mechanism 34 for reflector 38. This auxiliary interferometer 68 and associated detection electronics detects the phase difference of the auxiliary laser and maintains the optical path difference in the interferometer 22 for the coherent light source 14. This configuration results in the optical path difference in the interferometer 22 being maintained at a fixed value despite external mechanical vibrations or thermal drifts. The signal quality of the homodyne detection of the near-field microscope is enhanced. For example, FIG. 12 (a) shows the near-field image taken at infrared frequency of 1390 cm$^{-1}$ of two crossing BNNTs with phase stabilization. Compare this to FIG. 12 (b) which shows the same area at the same infrared frequency without phase stabilization scheme of FIG. 9. There are fewer imaging artifacts (streaks) are registered with phase stabilization switched on than it is switched off.

It will be appreciated that while the present method has been described and illustrated for measuring absorption spectra in the infrared using an infrared source 14, the present method may be readily adapted for measurement of absorption spectra in the visible in near ultraviolet (UV), however due to the longer wavelengths in the infrared the method is most suited to the infrared. Due to the shortness of the wavelengths in the higher visible and UV region, tighter focusing of the beams onto the nanoparticles is much easier.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An apparatus for measuring an absorption spectrum of nanoscale objects, comprising:
    a) a scanning atomic force microscope, a lock-in amplifier connected to said scanning atomic force microscope, a computer controller connected to said lock-in amplifier, a detector for detecting electromagnetic radiation connected to said lock-in amplifier, a coherent light source which emits a coherent beam of light;
    b) an interferometer integrated with said atomic force microscope, said coherent light source and said detector, said interferometer having a reference arm and a sample arm, the interferometer being positioned for directing light along the sample arm from said coherent light source to a sample mounted on a scanning stage of said scanning atomic force microscope and for directing a light beam scattered from the sample and a scanning probe tip of said atomic force microscope into said detector, said interferometer also being positioned for directing a light beam along the reference arm from said coherent light source to a position adjustable reflector and directing a light beam reflected from said adjustable reflector to recombine with said scattered light beam into said detector;
    c) a positioning mechanism for adjusting and maintaining a position of the adjustable reflector to give a relative optical phase difference between said light beams in said reference arm and said sample arm to be one of in a range from about $0.4\pi$ to about $0.6\pi$, or $-0.4\pi$ to about $-0.6\pi$;
    d) wherein said lock-in amplifier is configured to receive a reference frequency from said atomic force microscope and an output voltage signal from said detector and, based on said reference frequency and said output voltage signal, demodulate said output voltage signal into harmonic components and relaying second and higher harmonic components to said computer controller which is programmed with instructions to form an apertureless near-field scanning optical microscope image of said nanoscale objects.

2. The apparatus according to claim 1 wherein the optical phase difference between said light beams in said reference arm and said sample arm is adjusted to, and maintained at, about $0.5\pi$ or $-0.5\pi$.

3. The apparatus according to claim 1 wherein said positioning mechanism for adjusting and maintaining the adjustable reflector to give the optical phase difference between said light beams in said reference arm and said sample arm includes a position adjustment mechanism associated with said adjustable reflector, said position adjustment mechanism being connected to a feedback device which maintains the optical phase difference between the sample and reference arms.

4. The apparatus according to claim 2 wherein said positioning mechanism for adjusting and maintaining the adjustable reflector to give the optical phase difference between said light beams in said reference arm and said sample arm includes a position adjustment mechanism associated with said adjustable reflector, said position adjustment mechanism being connected to a feedback device which maintains the optical phase difference between the sample and reference arms.

5. The apparatus according to claim 3 wherein said feedback device includes a laser and associated detector, where said detector is positioned to measure a combined intensity of a laser light beam from said laser reflected from said sample and said adjustable reflector, and wherein said feedback device is configured to adjust a position of said reflector to maintain the same intensity on said detector.

6. The apparatus according to claim 4 wherein said feedback device includes a He—Ne laser and He—Ne detector, where said He—Ne detector is positioned to measure a combined intensity of the He—Ne laser light beam reflected from said sample and said adjustable reflector, and wherein said feedback device is configured to adjust a position of said reflector to maintain the same intensity on said He—Ne detector.

7. The apparatus of claim 1 wherein said coherent light source is an infrared light source.

8. The apparatus of claim 2 wherein said coherent light source is an infrared light source.

9. The apparatus of claim 5 wherein said coherent light source is an infrared light source.

10. The apparatus of claim 1 wherein said coherent light source is a visible light source.

11. The apparatus of claim 2 wherein said coherent light source is a visible light source.

12. The apparatus of claim 3 wherein said coherent light source is a visible light source.

13. The apparatus of claim 4 wherein said coherent light source is a visible light source.

14. A method of measuring an absorption spectrum of nanoscale objects, comprising:
    a) rastering a nanoscale object under a scanning probe tip of a scanning atomic force microscope;
    b) illuminating said nanoscale object and said scanning probe tip with a frequency tunable coherent light source along a sample arm of an interferometer;
    c) combining a scattered coherent light beam from said nanoscale object and said scanning probe tip along said sample arm with a beam of light from said frequency tunable light source reflected from an adjustable reflector in a reference arm of the interferometer and directing the combined coherent light beams into a detector;

d) demodulating an output signal from said detector to give second or higher harmonic demodulation signals and, using the second or higher harmonic demodulation signals, adjusting a position of the adjustable reflector to give an optical phase difference between said light beams in said reference arm and said sample arm to be in a range from about $0.4\pi$ to about $0.6\pi$, or from about $-0.4\pi$ to about $-0.62\pi$, and maintaining said position using feedback to maintain the optical phase difference; and e) obtaining an image of signal intensity being proportional to the imaginary part of infrared absorption coefficient of the sample through the combination of scanning probe microscopy and light scattering from a sharp scanning probe tip with said procedure of setting specific homodyne phase in the interferometer.

15. The method according to claim 14 wherein said optical phase difference is achieved by minimization of second or higher harmonic demodulation signals with adjustment of the position of the adjustable reflector when the scanning probe tip is on a sample location containing no resonances or on a metal substrate.

16. The method according to claim 14 wherein the optical phase difference between said light beams in said reference arm and said sample arm is adjusted to, and maintained at, about $0.5\pi$ or $-0.5\pi$.

17. The method according to claim 14 including adjusting and maintaining the adjustable reflector to give the optical phase difference between said light beams in said reference arm and said sample arm includes using a position adjustment mechanism associated with said adjustable reflector, said position adjustment mechanism being connected to a feedback device which maintains the optical phase difference between the sample and reference arms.

18. The method according to claim 17 wherein said feedback device includes a He—Ne laser and He—Ne detector, where said He—Ne detector is positioned to measure a combined intensity of the He—Ne laser light beam reflected from said sample and said adjustable reflector, and wherein said feedback device is configured to adjust a position of said reflector to maintain the same intensity on said He—Ne detector.

19. The method of claim 14 wherein said coherent light source is an infrared light source.

20. The method of claim 14 wherein said coherent light source is a visible light source.

21. The apparatus of claim 1 wherein the relative phase difference includes an absolute optical phase difference between said light beams in said reference arm and said sample arm, measured by an optical path length difference between the reference arm and said sample arm and divided by a wavelength of said coherent light source and multiplied by $2\pi$.

22. The apparatus according to claim 1 wherein said interferometer sample arm includes a focussing element for focusing light from said coherent light source onto the sample and the scanning probe tip of said atomic force microscope located in close proximity to the sample.

23. The apparatus according to claim 22 further comprising a feedback device including a laser and a light detector, a reflective surface in a fixed position with respect to said focussing element and an additional reflective surface mounted on a positioning mechanism that moves the additional reflective surface back and forth and which is tethered to said positioning mechanism for adjusting and maintaining a position of the adjustable reflector, wherein said laser, light detector, reflective surface, and additional reflective surface form an auxiliary interferometer adjacent to said interferometer, and wherein said light detector is positioned to measure an intensity of a laser light beam from said laser reflected from said reflective surface and said additional reflective surface, and whereas an optical phase difference measured for the laser light beam in said auxiliary interferometer is calculated and maintained by adjusting said positioning mechanism that is used to adjust the reflective surface in order to maintain the optical path length difference of the interferometer at a constant value during measurement.

24. The apparatus according to claim 1 wherein said coherent light source is a broadband infrared light source, and including a frequency selection device located at a position that is one of an output of said broadband infrared light source configured to select a specified frequency of light to be passed into the interferometer, and an input of said detector configured to select a specified frequency of light to be passed into the detector.

25. The apparatus according to claim 24 wherein said frequency selection device is any one of a filter and a Fourier Transform interferometer.

26. The apparatus according to claim 1 wherein said coherent light source is a frequency tunable narrow band coherent light source.

* * * * *